US010020083B1

(12) United States Patent
Heesch

(10) Patent No.: US 10,020,083 B1
(45) Date of Patent: Jul. 10, 2018

(54) SUPPORTED RADIATION PROTECTIVE GARMENT

(71) Applicant: Christian Martin Heesch, Spanish Fort, AL (US)

(72) Inventor: Christian Martin Heesch, Spanish Fort, AL (US)

(*) Notice: Subject to any disclaimer, the term of this patent is extended or adjusted under 35 U.S.C. 154(b) by 63 days.

(21) Appl. No.: 14/999,842

(22) Filed: Jul. 8, 2016

(51) Int. Cl.
*G21F 3/02* (2006.01)
*G21F 3/025* (2006.01)
*F16M 11/42* (2006.01)
*A41D 13/12* (2006.01)
*A41D 1/00* (2018.01)
*A61B 6/10* (2006.01)

(52) U.S. Cl.
CPC ............... *G21F 3/02* (2013.01); *A41D 1/005* (2013.01); *A41D 13/1209* (2013.01); *A61B 6/107* (2013.01); *A41D 2400/26* (2013.01)

(58) Field of Classification Search
USPC ............ 250/505.1, 515.1, 516.1, 519.1, 526; 211/85.13, 85.3, 85.8, 19, 20, 23
See application file for complete search history.

(56) References Cited

U.S. PATENT DOCUMENTS

| | | | | |
|---|---|---|---|---|
| 6,325,538 B1 * | 12/2001 | Heesch | ................ | A61B 6/107 128/846 |
| 7,973,299 B2 * | 7/2011 | Rees | ..................... | A61B 6/107 250/516.1 |
| 8,558,204 B2 * | 10/2013 | Rees | ..................... | A61B 6/107 250/516.1 |
| 8,674,330 B2 * | 3/2014 | Beck | ..................... | A61B 6/4423 211/85.29 |
| 9,349,492 B1 * | 5/2016 | Ganus | ..................... | G21F 3/03 |

* cited by examiner

*Primary Examiner* — Bernard Souw

(57) ABSTRACT

A supported radiation protective garment is presented that can be worn by a medical provider under a standard surgical gown during procedures that involve the use of radiation. When used by the provider, the protective garment is lifted by vertical support members which can be extended downward and retracted upward. Rolling or sliding means at the lower end of the vertical support members allow the provider to move unhindered while wearing the radiation protective garment. The provider has access to a control mechanism that allows the shifting between retracted and extended positions of the vertical support members without breaking sterility. An alternative embodiment presents an upper apron portion of the protective garment, which can be manually connected by an assistant to a lower rolling base portion. The invention allows the provider to wear a heavy protective garment, offering significantly better radiation protection than standard 'lead aprons', while not being burdened by the weight of the garment. Further, the invention allows to maintain sterility at all times, and gives two or more providers, each wearing this protective garment, the option to work and move in close spatial proximity to each other.

6 Claims, 8 Drawing Sheets

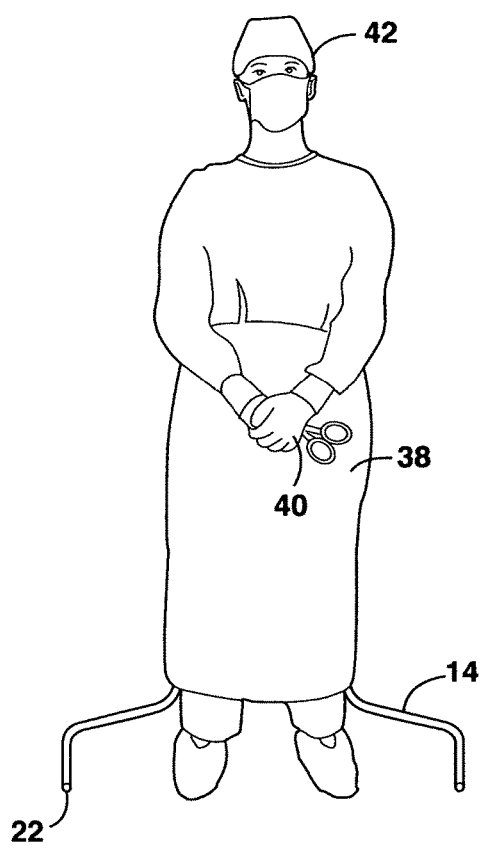
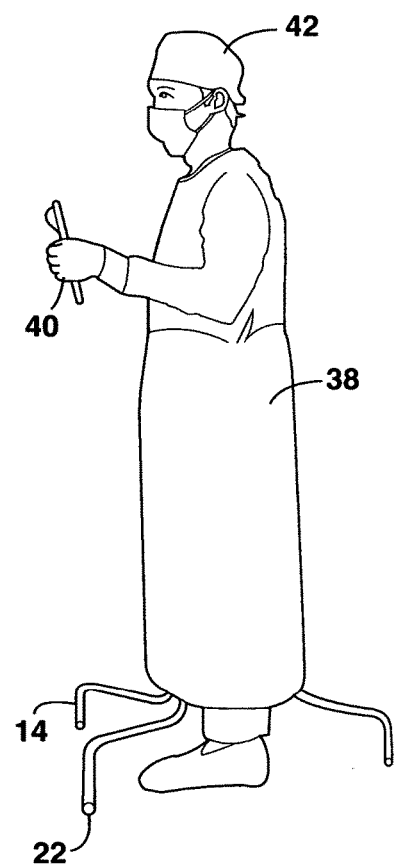
FIG. 6A  FIG. 6B

SUPPORTED RADIATION PROTECTIVE GARMENT

CROSS-REFERENCE TO RELATED APPLICATIONS

This is a non provisional patent application of U.S. Provisional Patent Application Ser. No. 62/282,788, filed Aug. 12, 2015.

Priority of U.S. Provisional Patent Application Ser. No. 62/282,788, filed Aug. 12, 2015, incorporated herein by reference, is hereby claimed.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates, in general, to radiation shields, and, in particular, to radiation protective garments that are worn by doctors, nurses, and other healthcare providers during medical or surgical procedures that involve the use of radiation.

2. General Background of the Invention

Some invasive medical or surgical procedures require the provider to not only wear sterile gowns and gloves, but also protective gowns or aprons to shield the provider from radiation. An incomplete list of examples of such invasive procedures that require simultaneous sterile attire of the operator and protection of the operator from radiation include cardiac catheterization and intervention, implantation and revision of cardiac pacemaker or defibrillator devices, vascular catheter based invasive and interventional procedures, abdominal surgery with radiographic assessment of the gallbladder and duct system, orthopedic surgery with implantation of joint replacement parts and radiographic control of the position of same, and many more.

Traditionally, physicians, nurses, and technicians performing such procedures wear heavy 'lead aprons', protective garments that absorb a substantial amount of radiation and leave the operator exposed to a limited amount of ionizing radiation that is felt to be acceptable. In reality, however, many providers are routinely exposed to radiation that exceeds the acceptable limits. Further, traditional radiation-protective garments are generally heavy and uncomfortable to wear. Their weight leads operators to sometimes choose a garment size that may not adequately protect the operator, especially since the detrimental effects of radiation are particularly important in the marrow of the long bones, where blood formation occurs. On the other hand, the regular wearing of heavy protective aprons has led to degenerative back problems in many an operator, leading some to stop doing procedures requiring radiation protection prior to retirement.

Over the past half century, many procedural changes and novel devices have been introduced to reduce both radiation exposure and weight load affecting the operator. Such changes include a reduction in the 'frame rate' of cineangiographic imaging sequences, the introduction of digital imaging technology, and changes in the material composition of protective aprons and coats, leading to a lighter weight. Nonetheless, an appropriately sized radiation protective apron continues to be heavy and uncomfortable to wear.

Description of the Prior Art

Several inventions have tried to tackle the problem without the above quoted changes in radiation exposure (which could adversely affect imaging quality) or protective material (which, when made lighter, may provide less protection from radiation). U.S. Pat. No. 6,325,538 to Heesch discloses a 'radiation field isolator apparatus', a flexible shield extending between the torso of the patient, the image intensifier, and the X-ray generator. The invention greatly reduces the amount of scatter radiation, and may make the wearing of protective lead aprons by medical personnel unnecessary. The disadvantage of this invention is that it requires existing catheterization laboratories, C-arms, and other X-ray equipment to be retrofitted.

U.S. Pat. No. 7,973,299 to Rees discloses a 'System and method for providing a suspended personal radiation protection system', whereby the operator's protective apron is supported by a ceiling-mounted rail system. Similar to the above Heesch patent, this system requires extensive retrofitting of existing X-ray suites, and the operator's radius of operation is limited by the extension of the rail system. Further, the majority of invasive procedures involving X-ray exposure require two operators, usually standing side-by-side, which would be difficult to achieve with Rees' proposed ceiling mounted rail system. U.S. Pat. No. 8,558,204, also to Rees, expands on his prior patent without overcoming the above listed problems and limitations.

U.S. Pat. No. 8,674,330 to Beck discloses a "Practical design for a walk-around, hands-free radiation protective shielding garment suspension apparatus". The described contraption puts the operator into a rolling framework which suspends a protective garment from the outside. The problem with the Beck invention is that it does not allow the operator to maintain sterility, owing to the spatial proximity of the bulky and non-sterile suspension apparatus to the protective apron and the operator's body. Further, the operators walking and moving space within the rolling apparatus is quite limited. Tripping and falling accidents seem likely, and may be severe.

Giving the above described problems and previously disclosed attempts to solve those, there appears to be a need to achieve the following goals simultaneously: a) effectively shield the operator during medical procedures from radiation, b) allow the operator to wear a sterile gown and maintain sterility, c) allow two operators to work side by side, d) minimize the chance of slipping and falling of the operator, and e) achieve all this without engaging in extensive and costly construction work in the X-ray facility and/or similarly extensive and costly retrofitting of currently existing X-ray equipment. The current invention addresses and resolves these problems.

BRIEF SUMMARY OF THE INVENTION

The present invention solves the problems confronted in the art in a simple and straightforward manner.

A protective coat or apron is provided, consisting of material similar to commercially available protective coats or aprons, although the material may be chosen thicker here, since weight is less of a concern. This will result in enhanced radiation protection for the operator.

The protective coat is structurally reinforced, providing internal support both vertically and horizontally. At three points, vertical support members are attached on the outside to the protective coat. In one embodiment of the invention, these support members can be extended and retracted, using a small motor connected to a power source located at the back of the protective coat. The operator dons the protective coat with the support members in their retracted position. After this, the operator undergoes the standard surgical hand washing and drying procedure. The operator then dresses in a surgical gown and gloves in the standard fashion. Following this, the operator extends the vertical support members, thereby slightly lifting the protective coat, taking all weight of the same off the shoulders of the operator. The vertical support members being equipped with rollable or slidable means at their lower ends, the operator can now move around in the catheterization laboratory or surgical suite. Sterility is maintained at all times. Should there be a need to leave the work area, the operator can retract the support means and walk normally.

There are numerous advantages to the present invention, as listed below:

1. The invention can be used in any existing catheterization laboratory, X-ray suite or operating room, without any need for structural changes of the room or the X-ray equipment.
2. The cost of this novel supported radiation protective garment is quite modest, compared to the devices disclosed in the prior art.
3. Weight not being a significant concern (the operator needs to carry the protective garment's weight only during those short periods when the vertical support members are in their retracted position), a thicker material can be chosen, significantly enhancing the radiation protection offered. Further, an arm extension, used at times by frequent operators to reduce radiation exposure to the left upper arm, which is located in proximity to the X-ray source, and which is not usually covered owing to weight concerns, can now be used without problems.
4. The device allows two or more operators to work side by side at a reasonable distance (unlike currently proposed ceiling-mounted support systems).

BRIEF DESCRIPTION OF THE SEVERAL VIEWS OF THE DRAWINGS

FIG. 6A represents a frontal perspective view of a physician wearing parts of the usual surgical attire over the present invention, with its vertical support members in an extended position and protruding inferiorly out of the surgical gown.

FIG. 6B represents a side perspective view of a physician wearing parts of the usual surgical attire over the present invention, with its vertical support members in an extended position and protruding inferiorly out of the surgical gown.

Figure 1:
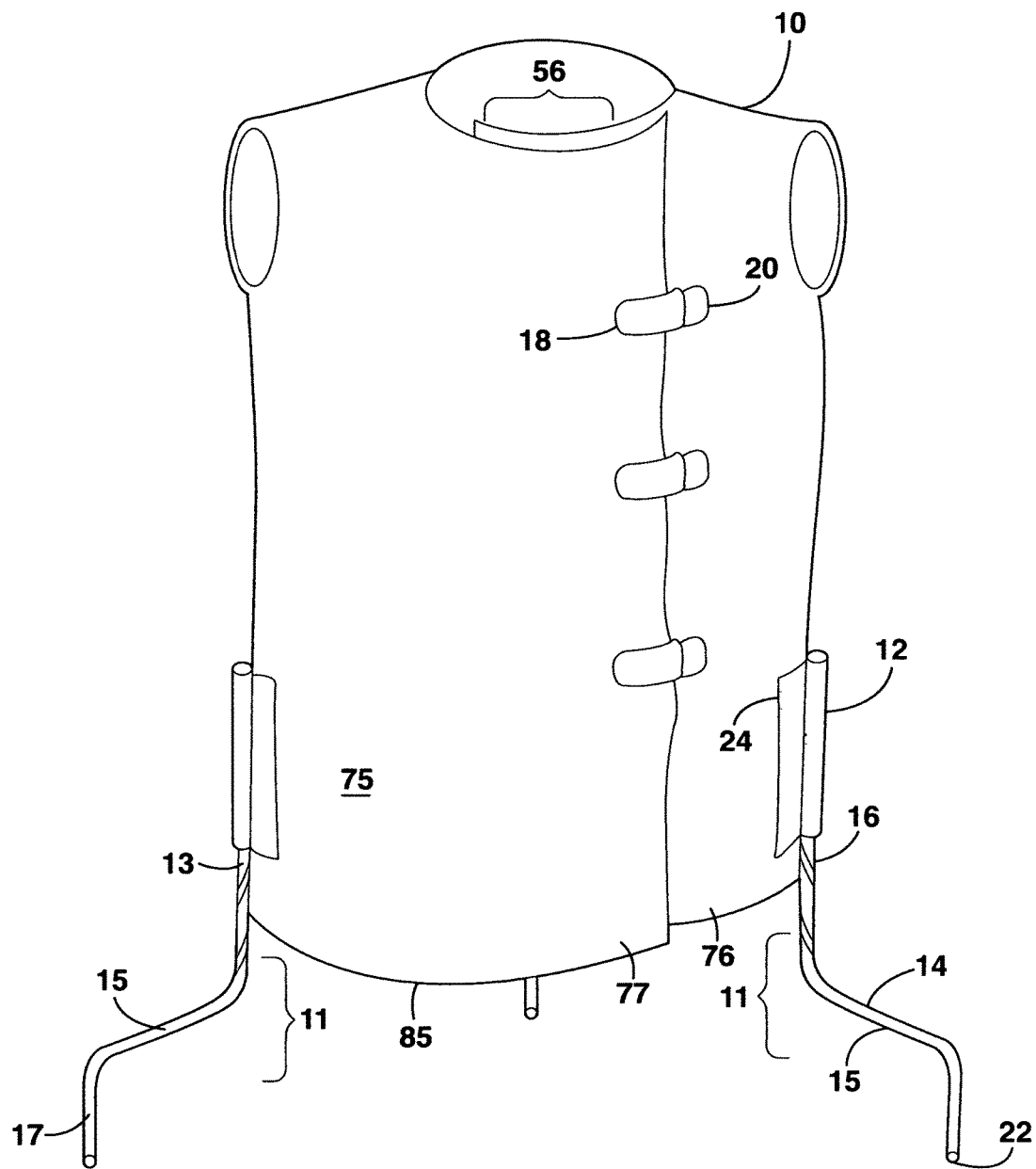
FIG. 1 is a perspective frontal view of one of the embodiments of the present invention, with the vertical support members in the extended position.

PARTS LIST 10 supported radiation protective garment, first embodiment
11 vertical support means
12 fixed portion of vertical support means 11
13 upper vertical part of extending portion 14 of vertical support means 11
14 extending portion of vertical support means 11
15 horizontal part of extending portion 14 of vertical support means 11
16 'lands and grooves' type surface of upper vertical part 13 of extending portion 14 of vertical support means 11 in one of the embodiments of the present invention
17 distal vertical part of extending portion 14 of vertical support means 11
18 closure buckle, male part
20 closure buckle, female part
22 rolling or sliding means of vertical support means 11
24 attachment part of the fixed portion 12 of the vertical support means 11
26 control button for vertical support member extension mechanism
28 battery pack
30 cable
32 electrical motor/air pump
34 air chamber
36 air seal
38 sterile gown
40 sterile gloves
42 medical provider
44 internal support member
46 apron part of second embodiment of the present invention
48 support base of the second embodiment of the present invention
50 joint member of support base 48
52 male connector of support base 46
54 female connector part of part 46
60 arrow showing outward extending motion of extending portion 14 of vertical support means 11
70 arrow showing inward retracting motion of extending portion 14 of vertical support means 11
75 radiation shielding cloth material
76 left edge of middle opening of supported radiation protective garment 10
77 right edge of middle opening of supported radiation protective garment 10
80 arrow showing upward retracting motion of extending portion 14 of vertical support means 11
85 lower rim of supported radiation protective garment 90 arrow showing downward extending motion of extending portion 14 of vertical support means 11

DETAILED DESCRIPTION OF THE INVENTION

FIG. 1 shows a first embodiment of the present invention, generally labeled 10. The operator dons protective garment 10 in the standard fashion, the front portion shows and area of overlap of the layers of protective garment 10, providing added protection. Standard male (18) and female (20) parts of a buckle closure mechanism are illustrated, a plurality of buckle closure mechanism is suggested. Toward the lower portion of protective garment 10, vertical support means 11 are shown, having an attachment part 24 with which they are firmly attached to the fabric of protective garment 10, a fixed portion 12 and an extending portion 14. Extending portion 14 is divided into an upper vertical part 13, a horizontal part 15, and a distal vertical part 17. At the caudal end of distal vertical part 17 rolling means 22 are provided. A variety of standard rolling or sliding means can be used, including but not confined to a wheel attached to a rotating joint (similar to the wheels of a shopping cart), a rolling metal ball housed with its upper part in a ball bearing, or other rolling or sliding means known in the art. Shown at 16 is also a 'lands and grooves' structuring on the surface of upper vertical part 13 of extending portion 14 of supporting means 11. The vertical support means 11 are shown in their extended position, with their horizontal part 15 and rolling means 22 pointing away from the center of protective garment 10, thereby preventing trip and fall injuries of the operator.

Figure 2:
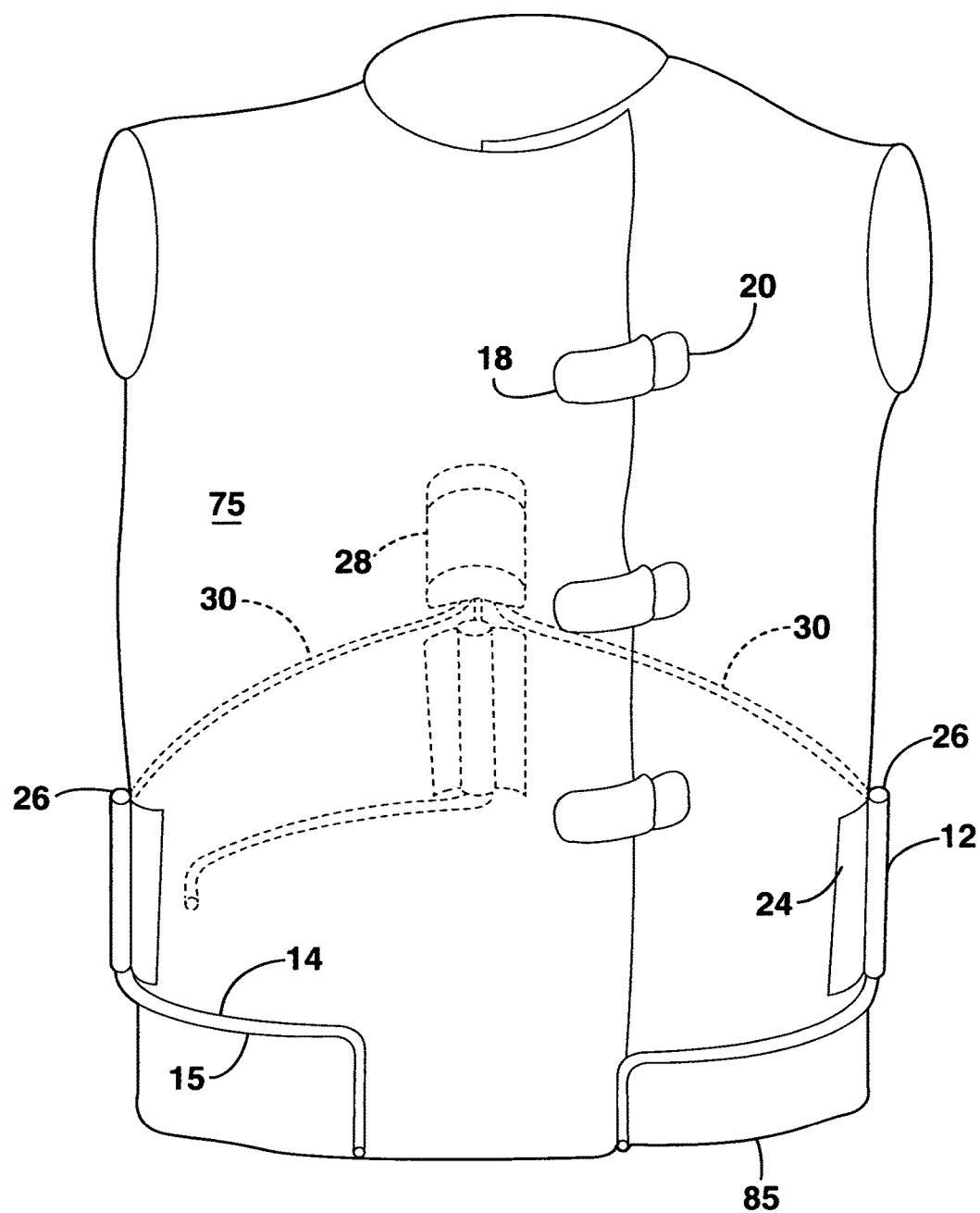
FIG. 2 is a perspective frontal view of one of the embodiments of the present invention, with the vertical support members in the retracted position.

FIG. 2 shows protective garment 10 with vertical support means 11 in the retracted position. In that position, the upper vertical part 13 of the extending portion 14 of vertical support means 11 is inside the fixed portion 12 of vertical support means 11. Horizontal part 15 of the extending portion 14 of vertical support member 11 is now situated adjacent to the lower rim of protective garment 10, a positional change achieved through the 'lands and grooves' type surface of the upper, vertically directed part 13 of extending portion 14 of vertical support member 11 that effects a rotational movement of extending portion 14 during retraction, and an inverse rotational movement of the same during extension. Note that there is a matching 'lands and grooves' type internal surface of the fixed portion 12 of vertical support member 11, which has not been depicted to avoid overcrowding of the illustration.

Figure 3:
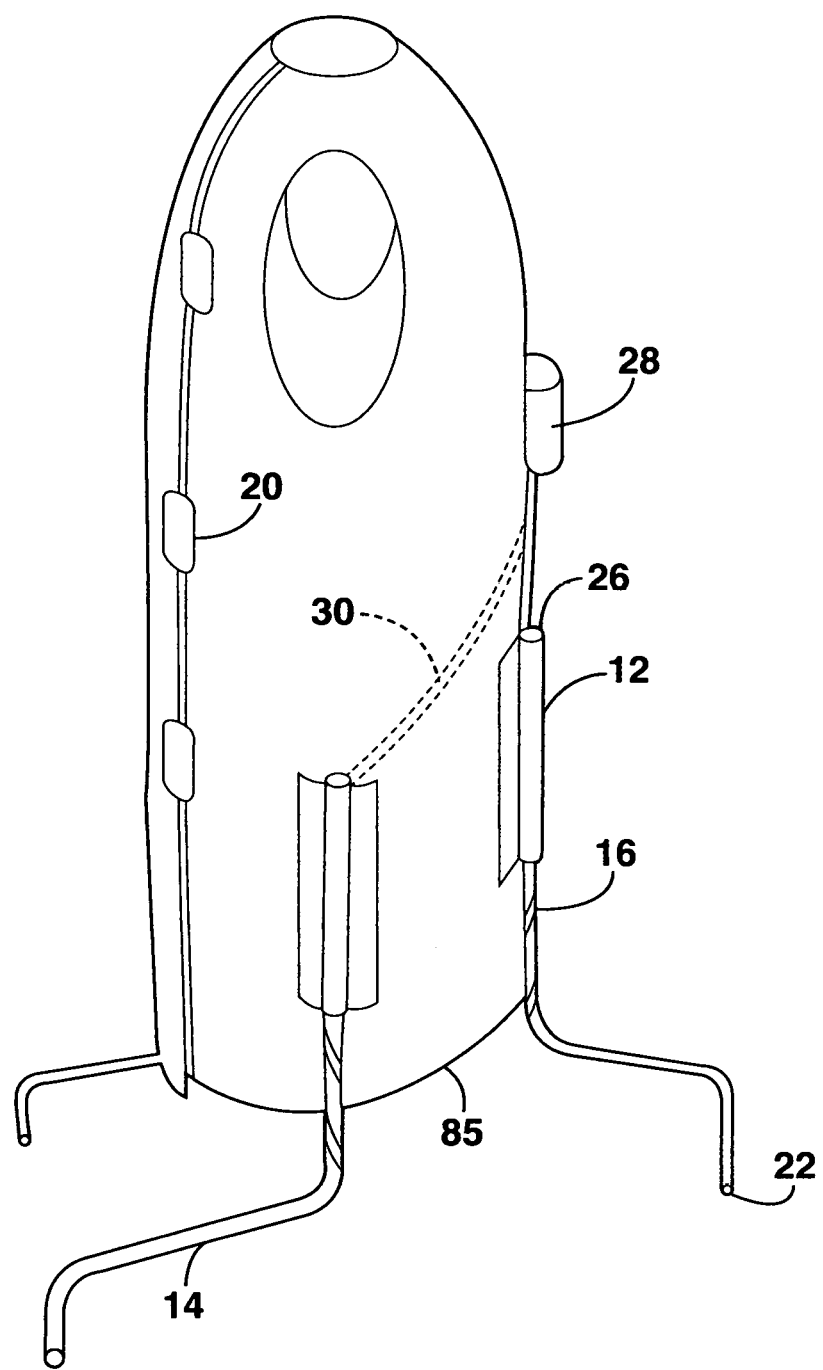
FIG. 3 is a perspective side view of one of the embodiments of the present invention, with the vertical support members in the extended position.

FIG. 3 shows protective garment 10 from the side, the extending portion 14 of vertical support means 11 is seen in the extended position, thereby providing lift support to the entire protective garment 10. Of note, garment size and operator size should be matched appropriately to ensure that, when extending portions 14 of support means 11 are in their extended position, a sufficient degree of lift' is provided to garment 10 to take all its weight off the shoulders of the operator, whereas, when extending portions 14 of support means 11 are in their retracted position, rolling means 22 should be sufficiently distanced from the ground to prevent the operator from tripping and falling. Obviously, in the retracted position, the entire weight of protective garment 10 will rest on the shoulders of the operator.

Figure 4:
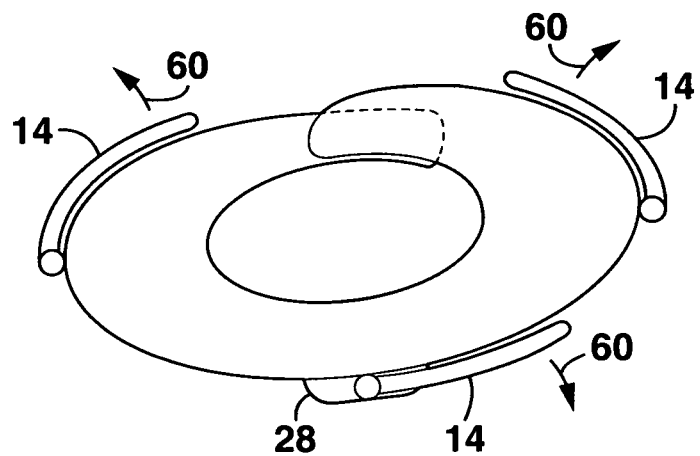
FIG. 4A represents a top view of one of the embodiments of the present invention, with the vertical support member in the retracted position.
FIG. 4B represents a top view of one of the embodiments of the present invention, with the vertical support member in the extended position.
Figure 4:
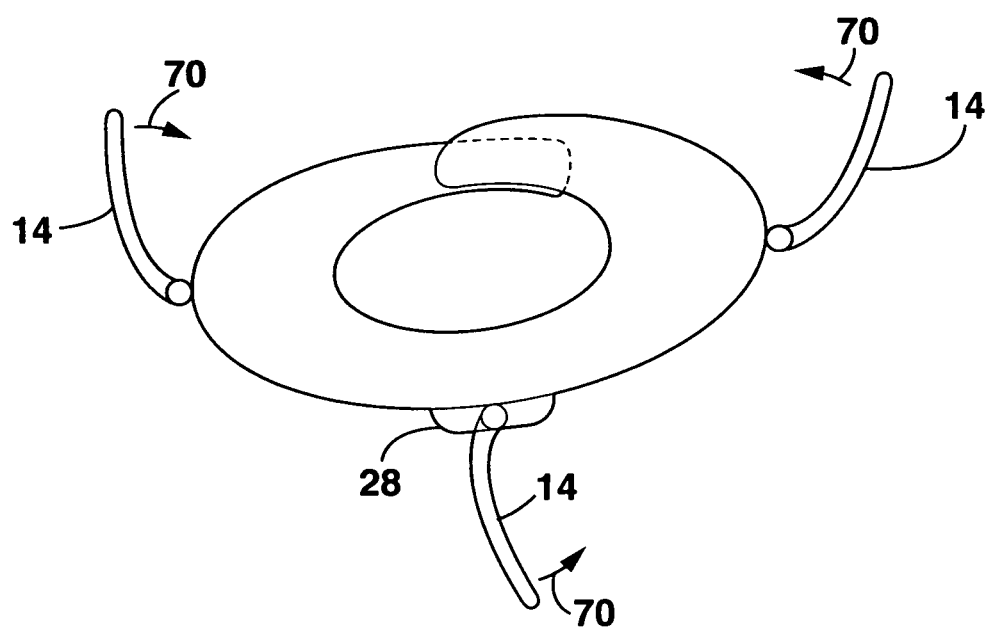

FIG. 4A provides a top view of protective garment 10, extending portions 14 of vertical support members 11 are in their retracted position. Arrows 60 indicate the horizontal direction of movement of extending portions 14 which will lead them to be in their extended position, as illustrated in FIG. 4B. Arrows 70 of that illustration indicate the horizontal direction of movement of extending portions 14 that will bring them back to their retracted position, as shown in FIG. 4A. Obviously, only the horizontal vectors of the movements of support means 11 during extension and retraction can be shown in this top view, a separated vertical vector (up or down) exists which is now shown in FIG. 5.

Figure 5:
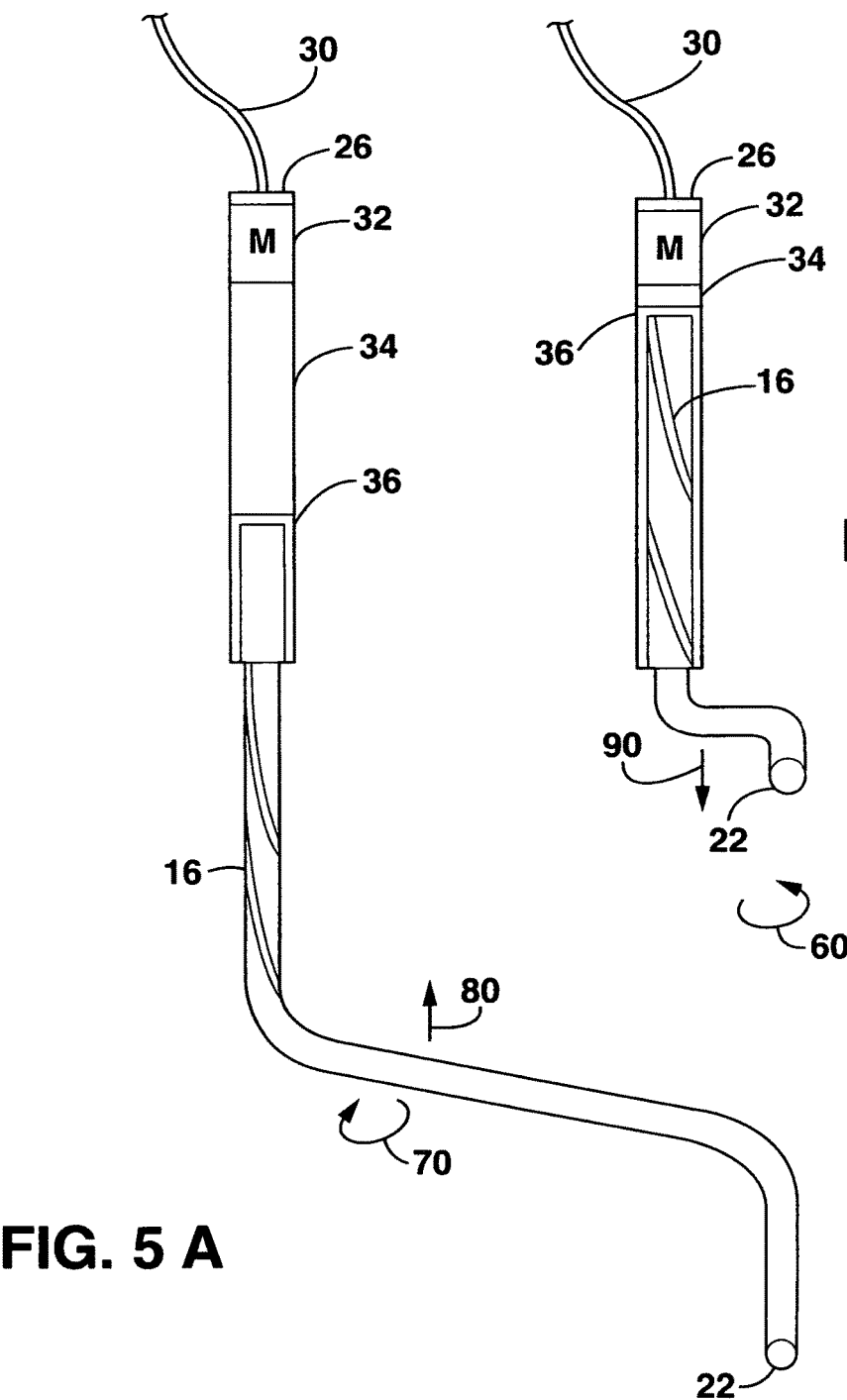
FIG. 5 is a schematic view of the motorized telescoping mechanism driving the positional change from extended to retracted of the vertical support members of one of the embodiments of the present invention.

FIGS. 5 A and B provide one of a myriad of possible driving mechanisms which can be used to effect a positional change of vertical support means 11 between their retracted and extended positions. In this illustration, to be understood as an example only, a small electrical motor driving an air pump (32) is housed in the upper part of fixed portion 12 of vertical support means 11. Motor/air pump 32, controlled by control button 26, is pumping air into air chamber 34, which has, at its distal end, air seal 32. Which the pumping of air into air chamber 32, upper vertical part 13 of extending portion 14 of vertical support means is pushed downward in relation to fixed portion 12 of vertical support means 11. Owing to the 'lands and grooves' external surface 16 of upper vertical part 13 and the corresponding internal surface (not depicted) of fixed portion 12 of vertical support means 11, extending portions 14 are pushed not only downward, but also rotated, thereby bringing horizontal part 15 and lower vertical part 17 from a position generally adjacent to the lower rim 85 of protective garment 10 (retracted position) into a position pointing away from the lower rim 85 of protective garment 10 (extended position), and also away from the feet of the operator. Arrow 80 shows the upwardly directed vertical vector of the retraction movement, arrow 90 shows the downwardly directed vertical vector of the extension movement, arrow 60 shows the outward horizontally rotating direction of the extension movement, and arrow 70 shows the inward horizontally rotating direction of the retracting movement. The mechanism is controlled through control button 26, which can be actuated by the provider sterilly through pushing movements through the sterile gown. One or more control buttons could be located at the top of one fixed portion 12 of vertical support means 11, a standard push-button or control mechanism can be used to make all support means 11 (which are cable 30 connected) move simultaneously and in the same direction, or individually. Cable 30 leads to battery pack 28 which could also house a control circuitry (not depicted). Further, a sterilly packable remote control unit (not depicted) could be set up to work with a small receiving unit (not depicted) connected to electric motors/air pumps 32 to allow their control in standard ways well known in the art.

Note that, by way of example, an electrical air pump, and 'lands and grooves' matching surfaces of the telescoping parts, are depicted here as ways to move and direct the support means. However, a multitude of standard driving and directional mechanisms (e.g. hydraulic mechanisms driven by an electric motor, one or a plurality of motors providing separate rotating and extending/retracting movements, purely mechanical systems pushing vertical support means 11 downward and outward either through the provider or through a support person etc. etc.) could all be employed without deviating from the scope of this invention. Note also that vertical support members 11 are depicted here in a curved fashion, reaching outwardly in their extended position in order to reduce the likelihood of trip and fall accidents, however, a simple straight or other design could also be employed, which would obviate the need for the rotational movement here suggested that occurs during extension and retraction of support means 11.

FIG. 6A is a front view of a medical provider 42 in surgical attire 38 (i.e. sterile gown and gloves, shown here with face mask). Below the sterile surgical attire the provider wears protective garment 10. Shown are the extending portions 14 of vertical support means 11 in their extended position—the provider should not feel any weight on his or her shoulders. FIG. 6B shows the same provider, surgical attire and protective garment from the side. Note that the provider can walk—rolling means 22 will ensure that protective garment 10 moves along with provider 42. Of note, lower vertical parts 17 of the extending portions 14 of vertical support means 11 have to be of sufficient length to allow provider 42 sufficient freedom of movement to prevent tripping and falling.

Figure 7:
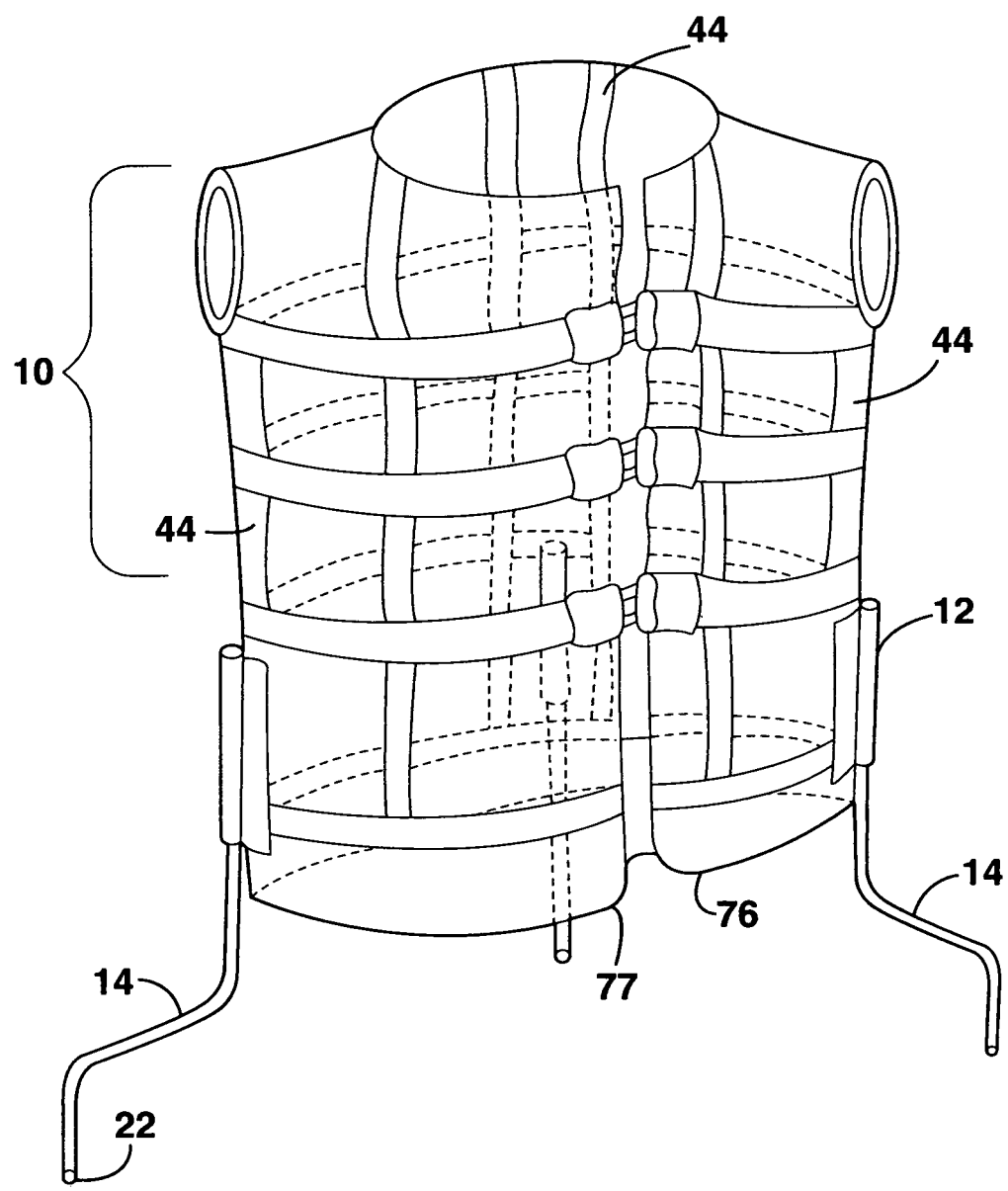
FIG. 7 represents a perspective view of an internal support structure for the present invention that provides vertical and horizontal support and can be used for various embodiments of the present invention.

FIG. 7 shows a suggestion of an internal support system for radiation shielding garment 10. Since garment 10 is lifted up in three areas, the remainder of the radiation protective material needs support in order to not sag around the provider, weighing him or her down in areas not directly at or adjacent to one of the fixed portions 12 of vertical support means 11. A 'corset' of internal support members 44, perhaps positioned between layers of radiation shielding material, is suggested as one option to achieve such internal structural stability. The ensemble of internal support members 44, in conjunction with the radiation shielding material 75 of garment 10 needs to provide maximum support against downward sagging of those portions of garment 10 which are far away from fixed portions 12 of vertical support means 11, while at the same time providing sufficient flexibility to allow for an easy outward bending of garment edges 76 and 77 so that provider 42 can easily don protective garment 10.

Figure 8:
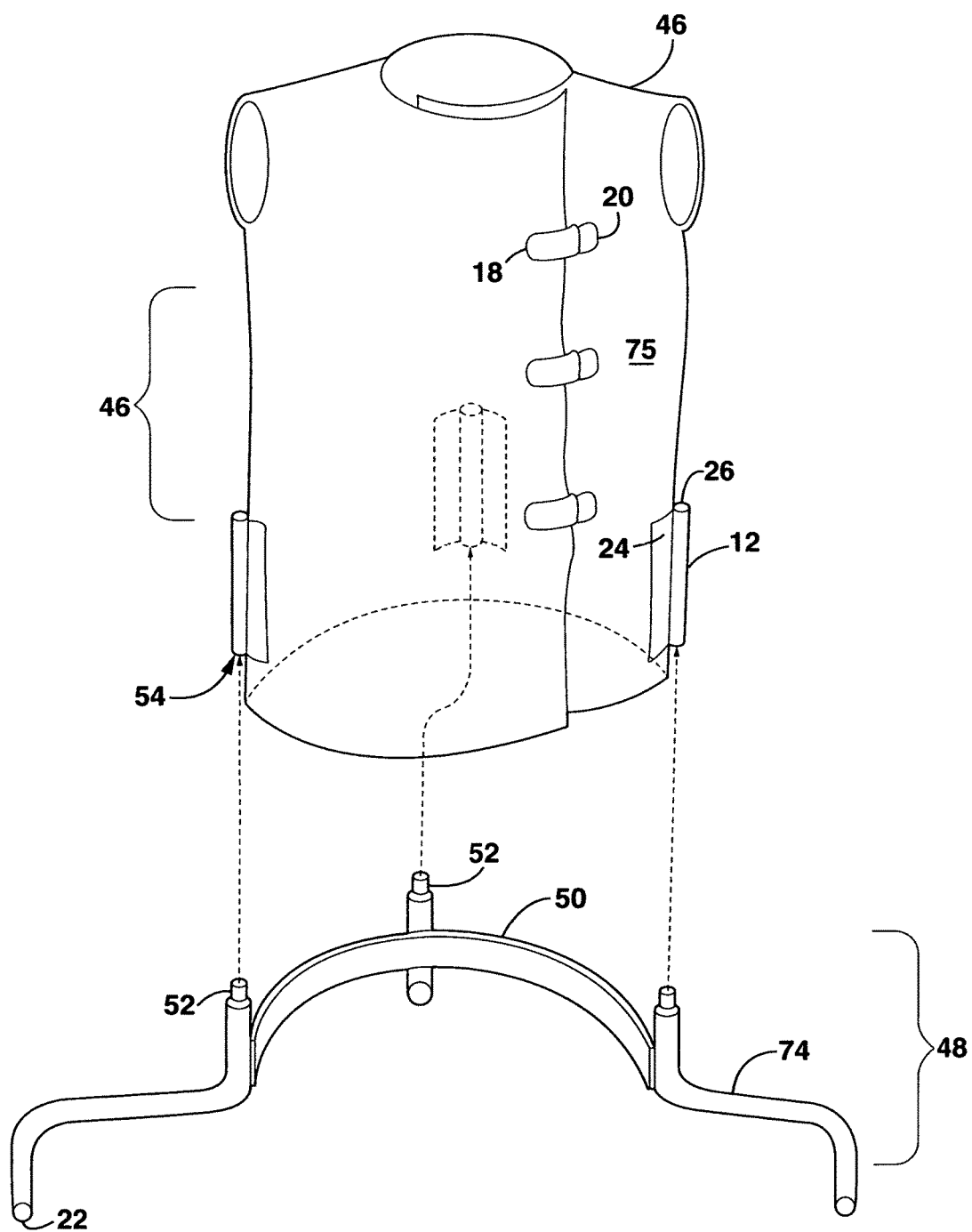
FIG. 8 represents a perspective, exploded view of an alternative embodiment of the present invention.

FIG. 8 shows a second embodiment of the supported radiation protective garment, divided into a 'protective apron part' 46 and a 'support base part' 48. The advantage of this embodiment is its simplicity. This embodiment has fixed portions 12 of vertical support means 11, but lacks extending portions 14 of vertical support means 11. Instead, at the lower end of fixed portions 12 are female connectors 54 of protective apron part 46. Support base 48 consists of semi-circular joint member 50 securely connecting a plurality of extending portions 74 of support base 48, said extending portions 74 having at their upper end male connectors 52 and at their lower end rolling means 22. Protective apron part 46 is donned by the provider in the standard fashion, whereupon the provider performs the standard surgical handwashing procedure (if a sterile procedure is planned), and dons the usual sterile gown. Following this, an assistant positions support base part 48 around the provider, so that provider stands in the semicircle of support base 48. The assistant then manually lifts each female connector onto one male connector 52, thereby putting apron part 46 into an elevated position in relation to provider 42, taking all weight off his or her shoulders.

The foregoing embodiments are presented by way of example only; the scope of the present invention is to be limited only by the following claims.

The invention claimed is:

1. A radiation shielding garment that can be worn by a medical provider under a sterile surgical gown during procedures that involve the use of radiation, said radiation shielding garment comprising:
   a. A garment made of material that provides significant protection from radiation;
   b. One or more vertical support means extending downwards from said garment towards the floor;
   c. Rollable or slidable means attached to the lower ends of at least one of said one or more vertical support means;
   d. Whereby said vertical support means lift and support said radiation shielding garment while said garment is being worn by said medical personnel.

2. The radiation shielding garment of claim 1, whereby said one or more vertical support means comprise two support means located anteriorly in relation to said medical provider and one support means located posteriorly in relation to said medical provider.

3. The radiation shielding garment of claim 1 or 2, whereby at least one of said one or more vertical support means can be reversibly extended downward and retracted upward.

4. The radiation shielding garment of claim 3, whereby said one or more vertical support means are configured to be able to shift their position between an upwardly retracted position generally adjacent to said radiation shielding garment and a downwardly extended position pointing away from said radiation shielding garment.

5. The radiation shielding garment of claim 2 or claim 3 or claim 4, whereby said one or more vertical support means can be reversibly extended and retracted by way of one or more electrical motors.

6. The radiation shielding garment of claim 1, whereby said one or more vertical support means can be reversibly attached to and disassembled from said radiation shielding garment while said radiation shielding garment is worn by said medical personnel.

* * * * *